United States Patent [19]

Berger et al.

[11] 4,150,031
[45] Apr. 17, 1979

[54] HYDROXY METHYL CARBAZOLE ACETIC ACID AND ESTERS

[75] Inventors: Leo Berger, Montclair; Alfred J. Corraz, Wayne; David R. Parrish, Glen Ridge; John W. Scott, Upper Montclair, all of N.J.

[73] Assignee: Hoffmann-La Roche Inc., Nutley, N.J.

[21] Appl. No.: 919,010

[22] Filed: Jun. 26, 1978

[51] Int. Cl.$^2$ ............................................. C07D 209/82
[52] U.S. Cl. .................................................... 260/315
[58] Field of Search ......................................... 260/315

[56] References Cited
U.S. PATENT DOCUMENTS 3,896,145   7/1975   Berger et al. ................... 260/315
4,057,640   11/1977  Biere et al. ..................... 260/315

OTHER PUBLICATIONS

Gore "Friedel–Crafts and Related Reactions", vol. III, pt. 1, pp. 94–95 (1964).
Sumpter et al., "The Chemistry of Heterocyclic Compounds", vol. 8, pp. 70–109 (1954).
Clemence et al., "J. Med. Chem.", vol. 9, p. 390 (1974).

Primary Examiner—Natalie Trousof
Assistant Examiner—R. W. Ramsuer
Attorney, Agent, or Firm—Jon S. Saxe; George M. Gould; William G. Isgro

[57] ABSTRACT

A process for the preparation of 6-chloro-α-methylcarbazole-2-acetic acid from 6-chloro-α-hydroxy-α-methylcarbazole-2-acetic acid and/or 6-chloro-α-methylene-2-carboxylic acid, is described. The preparation of intermediates, such as, 6-chloro-α-hydroxy-α-methylcarbazole-2-acetic acid and lower alkyl carbazole-2-oxalate, inter alia, is also described.

2 Claims, No Drawings

HYDROXY METHYL CARBAZOLE ACETIC ACID AND ESTERS

BRIEF SUMMARY OF THE INVENTION

In a first aspect, the invention relates to a process for preparing carbazole-2-oxalic acid lower alkyl ester by a process which comprises the steps of (a) acylating carbazole to yield a 9-alkanoylcarbazole, which is subsequently treated with a lower alkyl oxalyl halide to yield 9-alkanoylcarbazole-2-oxalic acid lower alkyl ester and (b) deacylating the product of step (a) to yield carbazole-2-oxalic acid lower alkyl ester.

In another aspect, the invention relates to the preparation of 6-chloro-α-hydroxy-α-methylcarbazole-2-acetic acid by a process which comprises the steps of (a) chlorinating a carbazole-2-oxalic acid lower alkyl ester to yield the corresponding 6-chlorocarbazole-2-oxalic acid lower alkyl ester; (b) treating the reaction product of step (a) with a Grignard reagent to yield a 6-chloro-α-hydroxy-α-methylcarbazole-2-acetic acid lower alkyl ester; and (c) treating the reaction product of step (b) with base to yield the desired 6-chloro-α-hydroxy-α-methylcarbazole-2-acetic acid.

Alternatively, the reaction product of step (a) can be treated with base to yield 6-chlorocarbazole-2-oxalic acid and subsequently treating said 6-chlorocarbazole-2-oxalic acid with a Grignard reagent or an alkyllithium to yield the desired 6-chloro-α-hydroxy-α-methylcarbazole-2-acetic acid.

In yet another aspect, the invention relates to the process of preparing 6-chloro-α-methylcarbazole-2-acetic acid by a process which comprises the steps of (a) treating 6-chloro-α-hydroxy-α-methylcarbazole-2-acetic acid with a dehydrating agent to yield 6-chloro-α-methylene-2-carbazole acetic acid; (b) hydrogenating the reaction product of step (a) to obtain the desired 6-chloro-α-methylcarbazole-2-acetic acid. Alternatively, the 6-chloro-α-hydroxy-α-methylcarbazole-2-acetic acid can be treated with stannous chloride in the presence of an alkanoic and mineral acid to yield the desired 6-chloro-α-methylcarbazole-2-acetic acid.

In still a further aspect, the invention relates to intermediates of the formulas

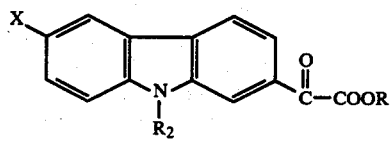
(a)

wherein R is hydrogen or lower alkyl, $R_2$ is hydrogen or

wherein $R_1$ is lower alkyl, and X is hydrogen or chlorine,

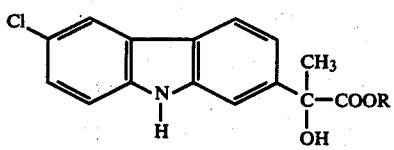
(b)

wherein R is hydrogen or lower alkyl, and

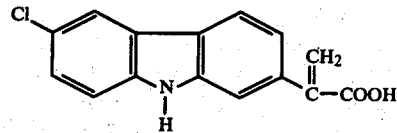
X

Formula (a) covers the compounds of formulas II, V, VI and VIII hereinafter, and formula (b) covers the compounds of formulas VII and IX, hereinafter.

DETAILED DESCRIPTION OF THE INVENTION

The invention relates to a process for preparing 6-chloro-α-methylcarbazole-2-acetic acid utilizing various sequential intermediates, as hereinafter described.

More specifically, the 6-chloro-α-methylcarbazole-2-acetic acid is prepared by utilizing a sequence of reaction steps, as hereinafter illustrated in Formula Schemes I, II and III, and further described.

FORMULA SCHEME I

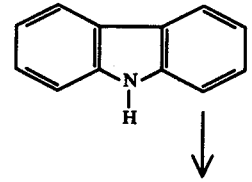
III

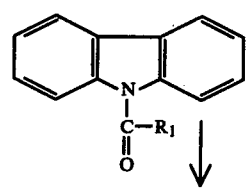
IV

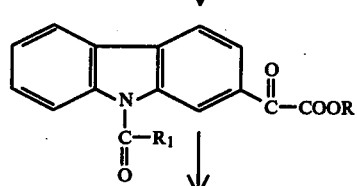
V

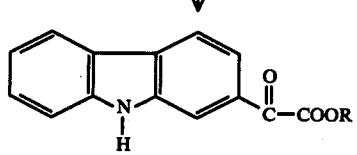
II wherein R and $R_1$ are lower alkyl.

As illustrated in Formula Scheme I, and in accordance with the invention, carbazole, the compound of formula III, is treated with an acylating agent, for example, an alkanoic anhydride, such as, acetic anhydride, propionic anhydride, or the like, in an inert organic solvent, for example, a halogenated alkane, such as methylene chloride, chloroform, or the like, in the presence of an inorganic acid, for example, hydrochloric acid, hydrobromic acid, sulfuric acid, or the like. The acylation is carried out at the reflux temperature of the reaction mixture. The resulting 9-lower alkanoylcarbazole, a compound of formula IV, is converted to the corresponding oxalate utilizing, for example, a lower alkyl oxalyl chloride, such as ethyl oxalyl chloride, in an inert organic solvent, for example, a halogenated alkane, such as methylene chloride, or the like, in the presence of a Lewis acid, for example, aluminum chloride, titanium tetrachloride, boron trifluoride, or the like. The reaction temperature of this latter step is preferably in the range of from about 0° C. to about 50° C.; most preferably in the range of from about 0° C. to about 25° C. Thereafter, the resulting 9-lower alkanoylcarbazole-2-oxalic acid lower alkyl ester of formula V is deacylated utilizing, for example, an inorganic acid, such as, sulfuric acid, hydrochloric acid, or the like, in an alkanol, such as methanol or ethanol, to yield the corresponding carbazole-2-oxalic acid lower alkyl ester of formula II. The deacylation is preferably carried out at a temperature in the range of about 10° C. to about 80° C.

pound of formula VII is hydrolyzed with base, that is, it is treated with, for example, an alkali metal hydroxide, such as, sodium hydroxide, potassium hydroxide or the like, in an inert organic solvent, for example, an alkanol, such as ethanol, methanol, or the like, to yield the 6-chloro-α-hydroxy-α-methylcarbazole-2-acetic acid of formula IX. Conveniently, the hydrolysis is effected at the reflux temperature of the reaction mixture.

Alternatively, the 6-chlorocarbazole-2-oxalic acid lower alkyl ester of formula VI can first be subjected to hydrolysis, as described above for the compound of formula VII, to obtain the 6-chlorocarbazole-2-oxalic acid characterized by formula VIII. The oxalic acid of formula VIII is then treated with a Grignard reagent, as discussed above for the conversion of the compound of

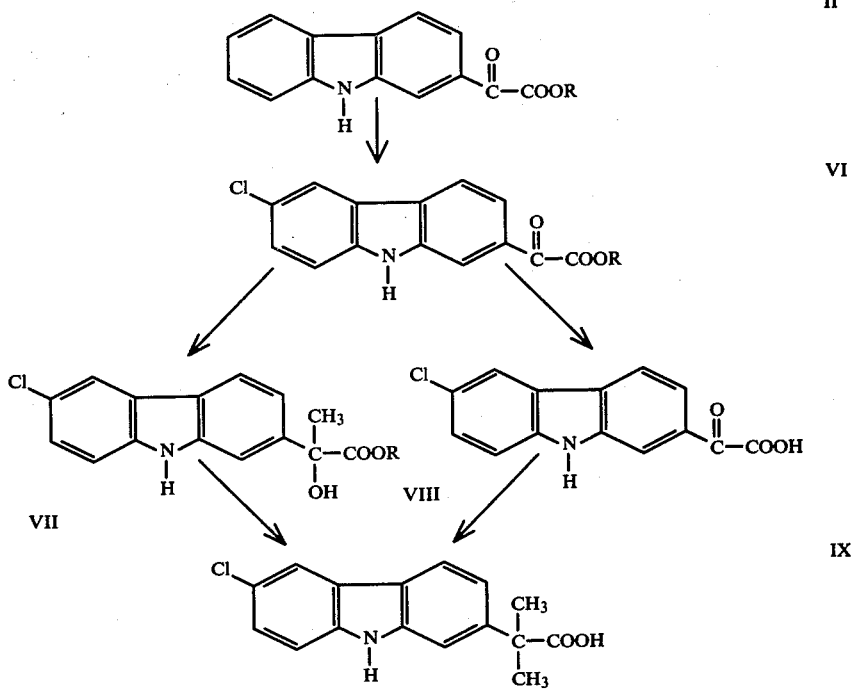

wherein R is lower alkyl.

Thereafter, as illustrated in Formula Scheme II, the carbazole-2-oxalic acid lower alkyl ester of formula II is chlorinated or treated with a chlorinating agent, such as, sulfuryl chloride in an inert organic solvent, such as, dimethylformamide or 1,2-dichloroethane. The chlorination can be carried out at the reflux temperature of the reaction mixture or at lower temperatures, for example, in the range of from −70° C. to reflux. Preferably, the chlorination is carried out at a temperature in the range of from about −40° C. to about −60° C. At low temperatures, selective chlorination, that is, chlorination at the 6-position, occurs. The resulting 6-chlorocarbazole-2-oxalic acid lower alkyl ester, a compound of formula VI, is reacted with a Grignard reagent, for example, a methylmagnesium halide or methyllithium, such as methylmagnesium iodide, methylmagnesium bromide, or the like, in the presence of an inert organic solvent, such as, tetrahydrofuran, ether or the like. The reaction is preferably carried out at a low temperature, for example, in the range of 0° to 10° C. The Grignard reaction yields the corresponding 6-chloro-α-hydroxy-α-methylcarbazole-2-acetic acid lower alkyl ester of formula VII. Thereafter, the comformula VI to the compound of formula VII. The Grignard reaction yields the compound 6-chloro-α-hydroxy-α-methylcarbazole-2-acetic acid of formula IX. If desired, the compound of formula IX can be separated by conventional procedures or can be utilized in situ in the reaction steps which follow.

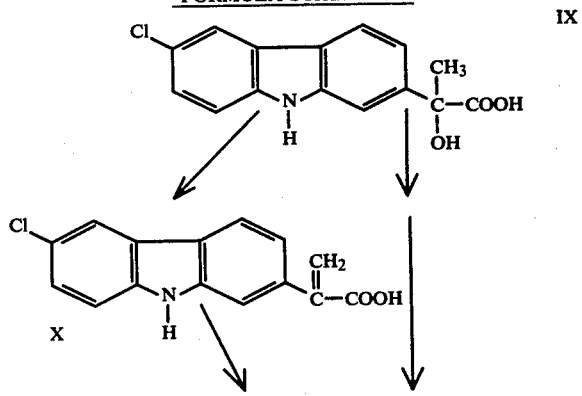

-continued
FORMULA SCHEME III

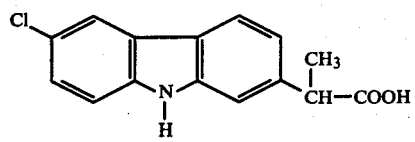

Finally, as illustrated in Formula Scheme III and in accordance with the invention, the 6-chloro-α-hydroxy-α-methylcarbazole-2-acetic acid of formula IX is treated with a dehydrating agent, for example, an inorganic acid, such as, hydrochloric acid, sulfuric acid, or the like, in an inert organic solvent, such as tetrahydrofuran, or the like. Conveniently, the dehydration is carried out at the reflux temperature of the reaction mixture. Subsequently, the resulting 6-chloro-α-methylene-2-carbazole acetic acid is treated with a hydrogenating agent, such as, hydrogen and platinum oxide or the like, in an alkanol, such as, methanol, ethanol, or the like, to yield 6-chloro-α-methylcarbazole-2-acetic acid, the compound of formula I.

Alternatively, the 6-chloro-α-hydroxy-α-methylcarbazole-2-acetic acid of formula IX can be subjected to hydrogenolysis utilizing, for example, an organic acid, for example, R—COOH, such as, glacial acid, propionic acid or the like, and an inorganic acid, such as, hydrochloric acid, and a compound, such as, stannous chloride, to yield 6-chloro-α-methylcarbazole-2-acetic acid in a single step.

The compound of formula I can be recovered from the reaction mixture by separation, such as filtration or the like. The compound of formula I is useful as an anti-inflammatory analgesic agent.

It is to be understood that in each of the reactions, as illustrated by Formula Schemes I, II and III, the intermediate materials that are produced may be separated or may be reacted in situ in the next reaction step. Also, the ratio of reactants is not critical. Preferably, however, equimolar ratios are utilized.

The Examples which follow further illustrate the invention. All temperatures are in degrees Centigrade, unless otherwise stated.

EXAMPLE 1

Preparation of ethyl carbazole-2-oxalate

To a stirred suspension of 167.2 g. of carbazole in 400 ml. of methylene chloride was added 103 ml. of acetic anhydride and 2.0 ml. of concentrated sulfuric acid. The mixture was degassed, placed under nitrogen and heated at reflux for 20 hours. The violet-colored solution was poured, after cooling to 20°, in a steady stream into a vigorously stirred solution of 175 g. of sodium bicarbonate in 1600 ml. of water. A color change to yellow-brown was accompanied by copious evolution of carbon dioxide. The mixture was stirred for 30 minutes and then the aqueous layer was extracted with 200 ml. of methylene chloride. The combined organic solutions were washed with 200 ml. of saturated sodium bicarbonate solution and dried over sodium sulfate. The sodium sulfate was removed by filtration and the filtrate was stirred for 1.0 hour with calcium chloride and 10 g. of Norite A. The mixture was filtered through Celite on medium sintered glass. The flask and funnel were washed with about 400 ml. of fresh methylene chloride to give a total filtrate of 1000 ml. of a 1 M solution of 9-acetylcarbazole. Such solutions appear to be stable indefinitely.

A mechanically-stirred suspension of 600 g. of aluminum chloride in 2000 ml. of methylene chloride was degassed, placed under nitrogen and cooled to 3° in an ice bath. A mixture of the 9-acetylcarbazole solution and 134 ml. of ethyl oxalyl chloride was added at a rate such that an internal temperature of 5° was maintained. This took about 2.0 hours and led to a deep red viscous mixture. The nitrogen inlet was disconnected and the system was vented to a gas scrubber to remove the hydrogen chloride gas. The ice bath was replaced by a 25° water bath. The bath temperature was raised to 45° over a 15 minute period as vigorous stirring was maintained to ensure a smooth evolution of the hydrogen chloride. The internal temperature rose to 35°—reflux— which was maintained for 1.0 hour.

The heating bath was removed and the mixture was stirred as 2000 ml. of ethanol was added at a rate such that a gentle reflux was maintained. This required 1.0 hour. The deep red mixture was then treated with 4000 ml. of 6 N hydrochloric acid at a rate such that gentle reflux continued. This required 1.0 hour, although the initial addition must be slow to control the exotherm. The two phase mixture was heated at reflux for 1.0 hour and cooled. The aqueous layer was extracted with 500 ml. of methylene chloride and the combined organic solutions were filtered through a layer of sodium sulfate. Solvent removal on a rotary evaporator at 50° gave crude ethyl 9acetylcarbazole-2-oxalate as a dark greenish crystalline solid.

A mixture of the crude ethyl 9-acetylcarbazole-2-oxalate, 1000 ml. of ethanol and 100 ml. of 6 N sulfuric acid was degassed, placed under nitrogen and heated at reflux for 1.5 hour. The homogeneous mixture was cooled to 20° and treated with 3000 ml. of water over a period of 1.0 hour. The resultant suspension was stirred an additional 30 minutes and filtered on coarse sintered glass. The solid was washed with 3000 ml. of water and air dried for 16 hours to give a tarnished gold colored solid. This free-flowing powder (still containing some water and inorganic salts) was heated at reflux with 3000 ml. of chloroform. A small amount of insoluble material and a small aqueous layer were observed. The mixture was filtered through Celite and extracted with 2000 ml. of 0.5 N sodium bicarbonate solution. The chloroform solution was stirred for 10 minutes with sodium sulfate and 25 g. of Norite A,* filtered through Celite, and stripped on a rotary evaporator at 60° to a volume of 800 ml. This mixture was warmed to effect solution and then stirred at ambient temperature as 3200 ml. of Skelly B was added over 1.0 hour. The resultant suspension was stirred at ambient temperature for 16 hours and filtered on coarse sintered glass. The solid was washed with 1000 ml. of 4:1 Skelly B**-chloroform. Air drying for 1.0 hour followed by drying to constant weight at 50°/0.1 mm. gave 181 g. of ethyl carbazole-2-oxalate as a gold powder, sintering at 130°, m.p. 130.5°–131.5°.

*carbon black **essentially n-hexane, bp 60°-68° C.

EXAMPLE 2

Preparation of ethyl 6-chlorocarbazole-2-oxalate

A solution of 267.28 g. of ethyl carbazole-2-oxalate in 2000 ml. of dimethylformamide was degassed, placed under nitrogen and cooled in a dry ice—ethanol bath to—42°. 95 Ml. of sulfuryl chloride was added over 1.25 hours as the temperature was maintained at −42° to −45°. The temperature was allowed to rise to about 0° over 1.0 hour and the solution was treated, over 1.0 hour, with 5000 ml. of water. The resultant suspension was stirred for 30 minutes and filtered on coarse sintered glass. The solid was washed with a total of 2000 ml. of water and air dried for 16 hours. The damp crude ethyl 6-chlorocarbazole-2-oxalate was taken up in 9500 ml. of chloroform at reflux, treated with 75 g. of Norite A and filtered through Celite on medium sintered glass. The flask and funnel were washed with about 2500 ml. hot chloroform until the filtrate was colorless. The combined filtrates were concentrated by distillation to a volume of 7600 ml. The solution was diluted with 7600 ml. of Skelly B, stirred at ambient temperature for 16 hours and filtered on coarse sintered glass. The solid was washed with 600 ml. of 1:1 chloroform-Skelly B, air dried 1.0 hour and then further dried to constant weight at 50°/0.1 mm. to give 228 g. of ethyl 6-chlorocarbazole-2-oxalate as fine yellow needles, m.p. 172.5°–173°.

EXAMPLE 3

Preparation of crude 6-chloro-α-methylcarbazole-2-acetic acid

A mixture of 75.43 g. of the ester of ethyl 6-chlorocarbazole-2-oxalate and 25 ml. of methanol was treated with a solution of 19.6 g. of potassium hydroxide in 375 ml. of water. The suspension was degassed, placed under nitrogen, stirred and heated at reflux for 1.0 hour to give an orange solution. Heating was stopped and the solution was treated with 200 ml. of water followed, over about 10 minutes, by 52.5 ml. of 6 N hydrochloric acid. The suspension was heated at reflux for 10 minutes to give a uniform red-orange slurry which was chilled in an ice bath for 30 minutes. The solid was collected on Whatman No. 541 paper, washed with a total of 750 ml. of water, air dried 16 hours, and then further dried to constant weight at 50°/0.1 mm (16 hours) to give crude 6-chloro-α-oxocarbazole-2-acetic acid as 67.5 g. of red-orange solid.

A suspension of 27.2 g. of magnesium turnings in 1125 ml. of tetrahydrofuran in a flask topped by a dry ice condenser was degassed and placed under nitrogen. 80 Ml. of methyl bromide was distilled into the flask over 1.0 hour. After about 10 minutes the Grignard reaction began as evidenced by a temperature rise. The flask was promptly chilled in an ice bath and the methyl bromide flow was controlled to maintain an internal temperature of 20° to 28°. The mixture was then stirred another 1.0 hour without cooling, by which time all of the magnesium had reacted.

A turbied solution of the crude oxalic acid of 6-chloro-α-oxocarbazole-2-acetic acid in 750 ml. of tetrahydrofuran was degassed, placed under nitrogen and cooled in an ice bath as the methylmagnesium bromide solution was added over 1.5–2.0 hours at a rate that maintained an internal temperature of <8° (gas evolution). The ice bath was left in place as the reaction mixture slowly came to room temperature overnight. The mixture was recooled in an ice bath and treated over 30 minutes with 250 ml. of 6 N hydrochloric acid at a rate such that the temperature was <15°. The mixture was treated with 500 ml. of saturated brine, stirred vigorously without cooling for 30 minutes, and filtered through coarse sintered glass. The flask and funnel were washed with 200 ml. of tetrahydrofuran. The aqueous layer of the filtrate was extracted with 200 ml. of tetrahydrofuran. The combined light yellow organic solutions were stripped on a rotary evaporator at 60° until free of tetrahydrofuran. The rapidly crystallizing residue was immediately suspended in 1000 ml. of water. This suspension was vigorously stirred for 1.0 hour to give a finely divided suspension which was filtered on Whatman No. 541 paper. The solid was washed with 4000 ml. of water. The washings removed a yellow oily impurity to give an off-white solid which was air dried over a weekend. Further drying at 50°/0.1 mm. for 4 hours caused a weight loss from 73 g. to give 72.8 g. of crude 6-chloro-α-hydroxy-α-methylcarbazole-2-acetic acid. Gc analysis of a similarly prepared sample showed it to contain 94.1% of 6-chloro-α-hydroxy-α-methylcarbazole-2-acetic acid, 5.4% of 6-chloro-α-methylene-2-carbazole-acetic acid and 0.5% of a compound of unknown structure.

To a suspension of the crude 6-chloro-α-hydroxy-α-methylcarbazole-2-acetic acid and 6-chloro-α-methylene-2-carbazole acetic acid in 1685 ml. of glacial acetic acid was added 225 g. of stannous chloride dihydrate. The mixture was degassed, placed under nitrogen, treated with 470 ml. of concentrated hydrochloric acid and heated in a 40° bath for 22 hours. After 4–5 hours, a clear brown solution resulted. Tlc showed that virtually all the 6-chloro-α-hydroxy-α-methylcarbazole-2-acetic acid had been converted to crude 6-chloro-α-methylcarbazole-2-acetic acid. To the solution of the 6-chloro-α-methylene-2-carbazole acetic acid and crude 6-chloro-α-methylcarbazole-2-acetic acid was added 185 mg. of platinum oxide which immediately dissolved to give a reddish solution. This material was loaded, with the aid of 50 ml. of acetic acid rinse, into a glass liner, pressurized to 500 psi with hydrogen and heated at 40° with rocking for 22 hours. The solution was removed from the liner with the aid of 50 ml. of acetic acid and diluted by the addition over 60 minutes of 3750 ml. of water. The resultant cream colored suspension was stirred with ice bath cooling for 2.0 hours and filtered on coarse sintered glass. The solid was washed with 2000 ml. of 2 N hydrochloric acid followed by 6000 ml. of water, air dried for 16 hours and further dried at 50°/0.1 mm. to give 65 g. of crude 6-chloro-α-methylcarbazole-2-acetic acid as an off-white powder, sintering at 205°, m.p. 207.5°–208°.

EXAMPLE 4

Purification of 6-chloro-α-methylcarbazole-2-acetic acid

A solution of a 62.5 g. sample of crude 6-chloro-α-methylcarbazole-2-acetic acid in 750 ml. of ethyl acetate was washed with 100 ml. and 200 ml. of 6 N hydrochloric acid and 200 ml. of saturated brine. The red-brown solution was dried over sodium sulfate, filtered through Celite and concentrated by distillation to the cloud point. Heating was stopped and 315 ml. of hexane was added over 2 minutes. The resulting suspension was stirred at 20° for 2 hours and filtered on coarse sintered glass. The solid was washed with a total of 250 ml. of hexane and air dried to give 56.25 g. of beige powder. This material was taken up in 225 ml. of ethanol at reflux and diluted with 1535 ml. of toluene. To the solution was added 28.2 g. of Norite 211 and the total was heated at reflux for 4.0 hours. The suspension was filtered through analytical grade Celite on medium sintered glass. About 250 ml. of hot ethanol-toluene was used to wash the filter cake. The clear, light yellow solution was concentrated by distillation to the cloud point (volume about 1300 ml.). The suspension was allowed to stand overnight, stirred a few minutes to break up the solid, and filtered on coarse sintered glass. The solid was washed with 200 ml. of toluene and dried at 50°/0.1 mm. to give 50.61 g. of cream-white microcrystalline solid, sintering from 204°, m.p. 207°-210°, which is 6-chloro-α-methylcarbazole-2-acetic acid.

EXAMPLE 5

Preparation of 9-acetylcarbazole

A stirred solution of 5 g. of carbazole, 50 ml. of chloroform, 5 ml. of acetic anhydride and 3 drops of concentrated sulfuric acid was heated under reflux (dry nitrogen atmosphere) for 5 hours. The reaction mixture was concentrated to dryness under reduced pressure and the residue was partitioned between ether and water. After the water was separated, the organic phase was washed by extraction with water (three times), dilute sodium bicarbonate (once) and water again (twice). Following drying of the ether solution over anhydrous magnesium sulfate, the desiccant was removed by filtration and the ether was evaporated; yielding 6.1 g., mp 76°-77°, of 9-acetylcarbazole.

EXAMPLE 6

Preparation of 9-acetylcarbazole-2-oxalic acid ethyl ester

Over the course of 2 hours, a solution of 20 g. of 9-acetylcarbazole, 16 g. of ethyloxalylchloride and 120 ml. of methylene chloride was added dropwise to a stirred, cooled (+3°) mixture of 60 g. of anhydrous aluminum chloride and 200 ml. of methylene chloride under an atmosphere of dry nitrogen. During the addition the temperature of the reaction mixture was held below +3° by means of an ice-water bath. After the addition the reaction mixture was stirred for 1 hour with the temperature going from +3 to +10, heated at reflux for ½ hour and poured onto a mixture of ice and concentrated hydrochloric acid. The aqueous mixture was extracted with methylene chloride (3×400 ml). The combined extracts were washed by extraction with water (8×200 ml) and dried over anhydrous granular sodium sulfate. Following filtration of the desiccant and evaporation of methylene chloride, a residue of 28.3 g. was obtained. The residue was triturated with ether, filtered and air dried to give 21.2 g. (71.4%), mp 101°-107°. A small portion recrystallized from methanol gave a m.p. of 108°-109°, and was 9-acetylcarbazole-2-oxalic acid ethyl ester.

EXAMPLE 7

Preparation of carbazole-2-oxalic acid methyl ester

A stirred solution of 6 g. of 9-acetylcarbazole-2-oxalic acid ethyl ester, 150 ml. of methanol and 2 ml. of concentrated hydrochloric acid (12 N) was heated at reflux for 5 hours and concentrated under reduced pressure to dryness. The residue was crystallized from methanol to give 4.6 g. (93.6%), m.p. 191°-193°, of carbazole-2-oxalic acid methyl ester.

EXAMPLE 8

Preparation of 6-chlorocarbazole-2-oxalic acid methyl ester

A solution of 1.1 ml. of sulfuryl chloride and 60 ml. 1,2-dichloroethane was added dropwise over the course of 45 minutes to a stirred, refluxing solution of 2.8 g. of carbazole-2-oxalic acid methyl ester in 300 ml. of 1,2-dichloroethane (under an atmosphere of dry nitrogen). After the addition the reaction mixture was refluxed and stirred an additional 20 minutes (tlc showed only a little starting material left and some dichloro present.). The reaction mixture was concentrated to dryness under reduced pressure. The residue was partitioned between ether and water. After the ether layer was separated, it was washed by extraction with water, dilute sodium bicarbonate and again water. Following drying of the ether solution over anhydrous magnesium sulfate, the desiccant was removed by filtration and the ether evaporated, yielding 3.0 g. Recrystallization from chloroform gave 1.75 g. (54.8%) (tlc showed some dichloro present). A second recrystallization from methanol yielded 1.3 g., mp 193°-193°, of 6-chlorocarbazole-2-oxalic acid methyl ester.

EXAMPLE 9

Preparation of 6-chloro-α-hydroxy-α-methylcarbazole-2-acetic acid

Over the course of 1 hour, a solution of 2.9 g. of methylmagnesium iodide [made from 0.42 g. of magnesium and 4.2 g. of methyl iodide (excess)] in 40 ml. of ether was added dropwise to a cooled (+2) stirring solution of 2 g. of 6-chlorocarbazole-2-oxalic acid methyl ester in 100 ml. of tetrahydrofuran. During the addition the reaction mixture temperature was held below +2 by means of an ice water bath. After the addition, the reaction mixture was stirred with no cooling for 1 hour, heated at reflux for 30 minutes and again cooled in an ice water bath. Water (60 ml.) containing 4 ml. of concentrated hydrochloric acid was added dropwise. The mixture was saturated with sodium chloride and extracted with ether (5×100 ml). The combined ether extracts were washed by extraction with water and dried over anhydrous magnesium sulfate. Following filtration of desiccant and evaporation of the ether, a residue of 2.5 g. remained. The residue was dissolved in 100 ml. of ethanol and 20 ml. of 3 N sodium hydroxide was added. After heating at reflux for 1 hour, the reaction solution was concentrated to dryness under reduced pressure. The residue was dissolved in 900 ml. of water and filtered through a Celite filter pad. A slight excess of concentrated hydrochloric acid was added to the filtrate and the liberated acid was extracted with ether (3×200 ml). The combined ether extract was washed with water and dried over anhydrous magnesium sulfate. Following filtration of the desiccant and evaporation of the ether 1.5 g. of a light yellow solid remained. The solid was triturated with chloroform and filtered; yielding 1.2 g. (59.6%). Recrystallization of 400 mg. of the crude acid afforded 206 mg., mp 218°-220°, of 6-chloro-α-hydroxy-α-methylcarbazole-2-acetic acid.

EXAMPLE 10

Preparation of 6-chloro-α-methylenecarbazole-2-acetic acid

A stirred solution of 0.4 g. of 6-chloro-α-hydroxy-α-methylcarbazole-2-acetic acid, 20 ml. of tetrahydrofuran and 0.8 ml. of concentrated sulfuric acid was heated at reflux for 22 hours. The reaction mixture was poured onto a mixture of ice and water and extracted with ether (3×100 ml). The ether extract was washed by extraction with water and dried over anhydrous magnesium sulfate. Following filtration of the desiccant and evaporation of the ether, a yield of 0.35 g. remained (tlc indicated an approximate 50/50 mixture of starting material and product). Crystallization from ethyl acetate gave 0.1 g. (12.0%)(tlc still starting material present). Recrystallization from methanol afforded 45 mg., mp 233°–234° (dec.), of 6-chloro-α-methylenecarbazole-2-acetic acid.

EXAMPLE 11

Preparation of 6-chloro-α-methylcarbazole-2-acetic acid

A mixture of 40 mg. of 6-chloro-α-methylenecarbazole-2-acetic acid, 50 ml. of ethanol and 30 mg. of platinum oxide was shaken in an atmosphere of hydrogen (initial pressure 54 lbs. per square inch) at room temperature. After 7 hours, the hydrogen uptake had stopped. The catalyst was filtered from the mixture and following evaporation of the ethanol the residue was crystallized from chloroform; yielding 13 mg. (32.3%), mp 184°–186° (dec.), the nmr of which was identical to an authentic sample of 6-chloro-α-methylcarbazole-2-acetic acid.

We claim:

1. A compound of the formula

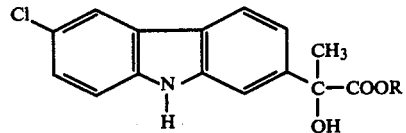

wherein R is hydrogen or lower alkyl.

2. A compound in accordance with claim 1, 6-chloro-α-hydroxy-α-methylcarbazole-2-acetic acid.

* * * * *

UNITED STATES PATENT AND TRADEMARK OFFICE
CERTIFICATE OF CORRECTION

PATENT NO. : 4,150,031
DATED : April 17, 1979
INVENTOR(S) : LEO BERGER ET AL.

It is certified that error appears in the above-identified patent and that said Letters Patent are hereby corrected as shown below:

Column 3, in Formula Scheme II,

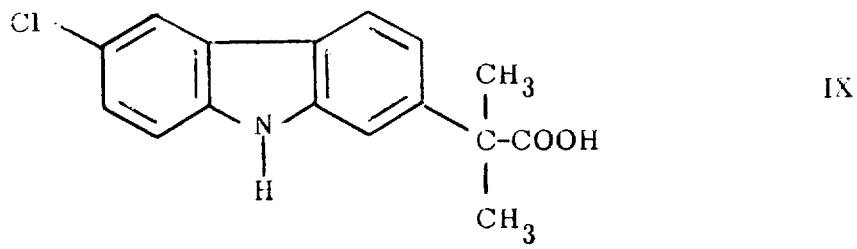

should be:

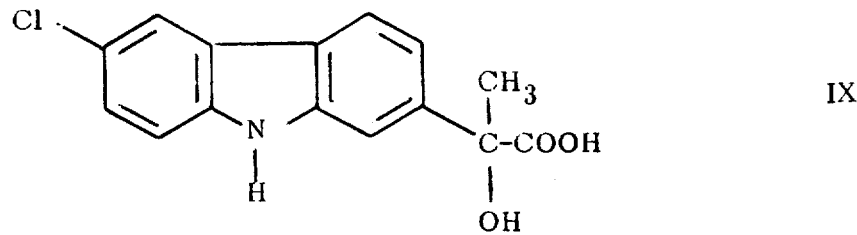

Signed and Sealed this

Thirteenth Day of January 1981

[SEAL]

Attest:

Attesting Officer

SIDNEY A. DIAMOND

Commissioner of Patents and Trademarks